United States Patent

Reiffenrath et al.

Patent Number: 5,151,213
Date of Patent: Sep. 29, 1992

[54] FLUORINE-CONTAINING AROMATIC COMPOUNDS

[75] Inventors: Volker Reiffenrath, Rossdorf; Ulrich Finkenzeller, Plankstadt, both of Fed. Rep. of Germany

[73] Assignee: Merck Patent Gesellschaft mit beschraenkter Haftung, Darmstadt, Fed. Rep. of Germany

[21] Appl. No.: 553,808

[22] Filed: Jul. 18, 1990

[51] Int. Cl.[5] .................. C09K 19/06; C09K 19/30; C09K 19/52
[52] U.S. Cl. .................. 252/299.6; 252/299.63; 252/299.01; 570/129
[58] Field of Search .................. 252/299.62, 299.63; 570/129

[56] References Cited

U.S. PATENT DOCUMENTS

| | | | |
|---|---|---|---|
| 4,122,026 | 10/1978 | Osman | 252/299.61 |
| 4,431,263 | 2/1984 | Garito | 350/96.34 |
| 4,439,514 | 3/1984 | Garito | 430/272 |
| 4,595,521 | 6/1986 | Petrzilka et al. | 252/299.61 |
| 4,767,826 | 8/1988 | Liang | 525/421 |
| 4,871,469 | 10/1989 | Reiffenrath et al. | 252/299.61 |
| 4,886,619 | 12/1989 | Janulis | 252/299.1 |
| 4,925,590 | 5/1990 | Reiffenrath | 252/299.61 |
| 4,961,874 | 10/1990 | Takeuchi et al. | 252/299.6 |

FOREIGN PATENT DOCUMENTS

| | | |
|---|---|---|
| 3902328 | 8/1990 | Fed. Rep. of Germany. |
| 8802357 | 4/1988 | World Int. Prop. O.. |
| 8807516 | 10/1988 | World Int. Prop. O.. |

Primary Examiner—Robert L. Stoll
Assistant Examiner—C. Harris
Attorney, Agent, or Firm—Millen, White & Zelano

[57] ABSTRACT

Fluorine-containing aromatic compounds of the formula I

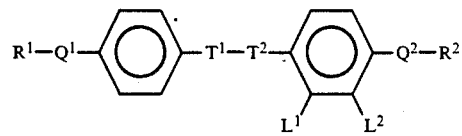

in which
$R^1$ is alkyl having up to 12 C atoms or alkenyl having 2 to 12 C atoms,
$Q^1$ and $Q^2$ are each, independently of one another, —O— or a single bond, and one of the radicals $Q^1$ and $Q^2$ is alternatively trans-1,4-cyclohexylene,
$T^1$ is

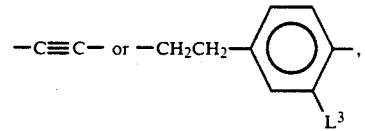

$T^2$ is

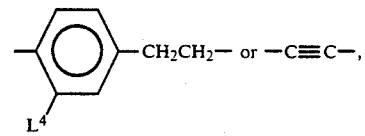

$R^2$ is F, Cl, —CF$_3$, —OCF$_3$, —OCHF$_2$ or one of the meanings of $R^1$, and
$L^1$, $L^2$,
$L^3$ and $L^4$ are each H or F,
are suitable as components of liquid-crystalline phases for IR shutters.

6 Claims, No Drawings

FLUORINE-CONTAINING AROMATIC COMPOUNDS

SUMMARY OF THE INVENTION

The invention relates to fluorine-containing aromatic compounds of the formula I

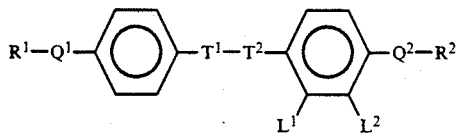

in which
$R^1$ is alkyl having up to 12 C atoms or alkenyl having 2 to 12 C atoms,
$Q^1$ and $Q^2$ are each, independently of one another, —O— or a single bond, and one of the radicals $Q^1$ and $Q^2$ is alternatively trans-1,4-cyclohexylene,
$T^1$ is

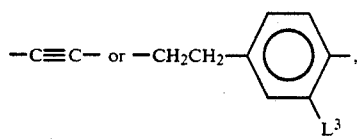

$T^2$ is

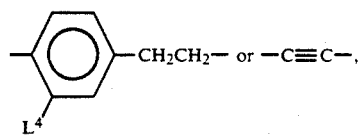

$R^2$ is F, Cl, —$CF_3$, —$OCF_3$, —$OCHF_2$ or one of the meanings of $R^1$, and
$L^1$, $L^2$,
$L^3$ and $L^4$ are each H or F,
and the use thereof as components of liquid-crystalline phases.

For reasons of simplicity, Phe below is an unsubstituted 1,4-phenylene group, PheX is a 1,4-phenylene group which is monosubstituted or disubstituted by fluorine, and Cy is a trans-1,4-cyclohexylene group.

The compounds of the formula I can be used as components of liquid-crystalline phases, in particular for displays based on the principle of the twisted cell (including supertwist cells, such as SBE, STN, OMI etc.), the guest-host effect, the effect of deformation of aligned phases or the effect of dynamic scattering. Compounds of the formula I are preferably also suitable for use as components in liquid-crystalline phases for displays based on the ECB effect.

Similar compounds are described by B. Grant, Mol. Cryst. Liq. Cryst. 48, 175 (1978). However, these do not contain any fluorine substituents.

The invention had the object of finding novel liquid-crystalline or mesogenic compounds which are suitable as components of liquid-crystalline phases. This object was achieved by the provision of the compounds of the formula I.

It has been found that the compounds of the formula I are preeminently suitable as components of liquid-crystalline phases. In particular, they can be used to prepare liquid-crystalline phases having extremely high optical anisotropy and particularly favorable elastic properties. The substances of the formula I are therefore particularly preferably suitable for use in mixtures for IR shutters.

Suitable mixtures must be carefully optimized for the particular cell type, the elastic properties (for example $K_3/K_1$, $K_3/K_2$), in particular, having a crucial effect in determining the optical properties, and compounds having high birefringence likewise being advantageous.

For industrial use in electrooptical display elements, LC phases are required which must satisfy a large number of requirements. LC phases which can be used in industry are required to have a liquid-crystalline mesophase in a suitable temperature range and a low viscosity, in particular even at low temperatures.

Surprisingly, it became apparent that the addition of compounds of the formula I gives liquid-crystalline phases which satisfy the abovementioned criteria in an excellent manner.

The compounds according to the invention are distinguished, compared with the compounds of the prior art, by particularly favorable combinations of desired material parameters.

In addition, the provision of the compounds of the formula I extends the range of liquid-crystalline substances which are suitable from various applicational points of view for the preparation of nematic mixtures.

The compounds of the formula I have a broad field of application. Depending on the choice of substituents, these compounds can be used as base materials from which liquid-crystalline phases are predominantly composed; however, it is also possible to add compounds of the formula I to liquid-crystalline base materials from other classes of compound, in order, for example, to optimize the dielectric and/or optical anisotropy of a dielectric of this type. The compounds of the formula I are furthermore suitable as intermediates for the preparation of polymers and of other substances which can be used as constituents of liquid-crystalline phases.

The optimization of the compounds of the invention for various uses, by selection of substituents, is in accordance with the principles well known to those skilled in the art.

In the pure state, the compounds of the formula I are colorless and form liquid-crystalline mesophases in a temperature range which is favorable for electroopical use.

The invention thus relates to the compounds of the formula I, and to the use of these compounds as components of liquid-crystalline phases. The invention furthermore relates to liquid-crystalline phases containing at least one compound of the formula I, and to liquid-crystal display elements, in particular electrooptical display elements, which contain phases of this type.

Above and below, $R^1$, $Q^1$, $L^1$, $L^2$, $L^3$, $L^4$, $Q^2$ and $R^2$ are as defined, unless expressly stated otherwise.

The compounds of the formula I include preferred bisphenylbutadiynes of the formula Ia

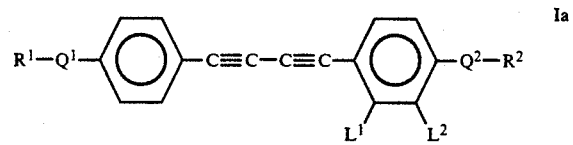

in which $R^1$ is alkyl having up to 12 C atoms or alkenyl having 2 to 12 C atoms, $Q^1$ and $Q^2$ are each, independently of one another, —O— or a single bond, and one of the radicals $Q^1$ and $Q^2$ is alternatively trans-1,4-cyclohexylene, $R^2$ is F, Cl, —$CF_3$, —$OCF_3$, —$OCHF_2$ or one of the meanings of $R^1$, and one of the radicals $L^1$ and $L^2$ is F and the other of these radicals is H or F.

The compounds of the formula Ia include preferred bisphenylbutadiynes in which $L^1$ is H, $L^2$ is F, $Q^2$ is a single bond and $R^2$ is F, $CF_3$, —$OCF_3$, —$OCHF_2$, and preferred bisphenylbutadiynes in which $L^1 = L^2 = F$ and $R^2$ is alkyl, and $Q^2$ is preferably —O—.

The compounds of the formula I furthermore include preferred tolans of the formulae Ib and Ic

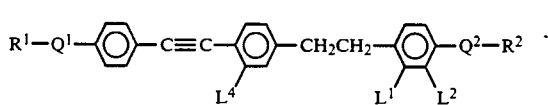

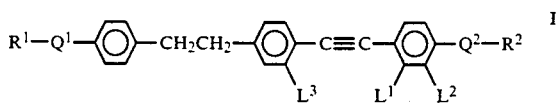

and preferred aromatic compounds of the formula Id

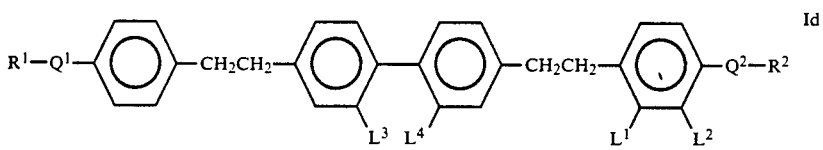

in which $R^1$, $Q^1$, $Q^2$, $R^2$, $L^1$, $L^2$, $L^3$ and $L^4$ are as defined in claim 1.

Particular preference is given to bisphenylbutadiynes of the formula Ia in which $R^1$ is n-alkyl, $Q^1$ and $Q^2$ are each a single bond, and $L^1$, $L^2$ and $R^2$ are as defined in the table below:

| $L^1$ | $L^2$ | $R^2$ |
|---|---|---|
| H | H | F |
| H | F | F |
| H | H | $CF_3$ |
| H | H | —$OCF_3$ |
| H | H | —$OCHF_2$ |
| F | F | —O-alkyl |
| F | F | -alkyl |

Furthermore, preference is given to the analogous butadiynes in which $Q^1$ is trans-1,4-cyclohexylene.

$R^2$ is preferably F, Cl, $CF_3$, —$OCF_3$ or —$OCHF_2$. Preferred compounds of the formula I are those in which at least one, preferably two, of the radicals $L^1$ to $L^4$ is F. One of the radicals $L^1$ and $L^2$ (preferably $L^2$) or alternatively both the radicals $L^1$ and $L^2$ is preferably fluorine.

Particular preference is given to the compounds of the formula Ic in which $R^1$ is n-alkyl, $Q^1$ is a single bond or trans-1,4-cyclohexylene, $Q^2$ is a single bond, and $L^1$, $L^2$, $L^3$ and $R^2$ are as defined in the table below.

| $L^1$ | $L^2$ | $L^3$ | $R^2$ |
|---|---|---|---|
| H | H | H | F |
| H | H | H | Cl |
| H | H | H | $CF_3$ |
| H | H | H | $OCF_3$ |
| H | H | H | $OCHF_2$ |
| H | F | H | F |
| H | F | H | Cl |
| H | F | H | $OCHF_2$ |
| F | H | H | -alkyl |
| H | H | F | -alkyl |

Likewise, preference is given to the compounds of the formula Id in which $R^1$ and $R^2$ are n-alkyl, $Q^1$ and $Q^2$ are single bonds or one of the radicals $Q^1$ and $Q^2$ is alternatively —O—, and $L^1$ to $L^4$ are as defined in the table below.

| $L^1$ | $L^2$ | $L^3$ | $L^4$ |
|---|---|---|---|
| F | H | H | H |
| H | F | H | H |
| H | H | F | H |

The compounds of the formula I can be prepared by conventional methods, as described, for example, in the literature (for example in the standard works, such as Houben-Weyl, Methoden der Organischen Chemie [Methods of Organic Chemistry], Georg-Thieme-Verlag, Stuttgart), the reaction conditions being chosen, in particular, to match those which are known and suitable for the reactions mentioned. Use may also be made here of variants which are known per se, but are not described here in greater detail.

If desired, the starting materials can also be formed in situ by not isolating them from the reaction mixture, but instead reacting them further to form the compounds of the formula I.

Thus, the compounds of the formula Ia can be prepared by reacting a compound of the formula II

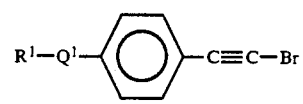

in the presence of a Cu catalyst with a compound of the formula III

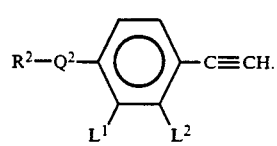

Cadiot-Chodhiewicz coupling reactions of this type are described in Houben-Weyl, Volume 5/2a, p. 931 ff.

The starting compounds of the formulae II and III can be prepared by known processes (Houben-Weyl, Volume 5/2a).

Preferred synthetic methods for the compounds of the formulae Ib, Ic and Id are shown in schemes 1 to 4 below. In addition, these compounds can be prepared by a number of further processes analogously to similar, known compounds:

Scheme 1:

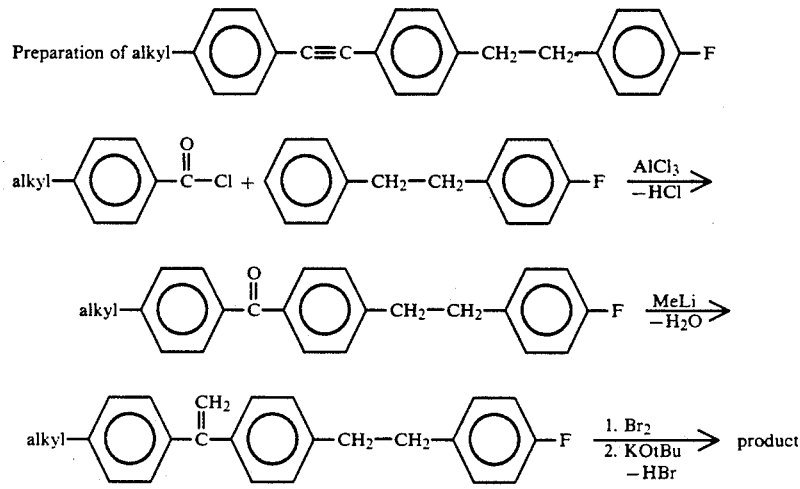

Scheme 2:

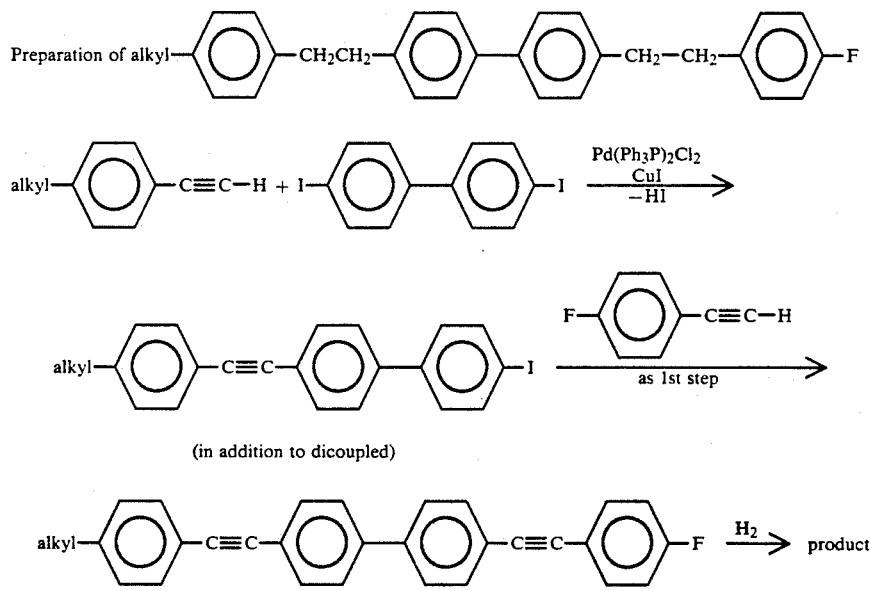

Scheme 3:

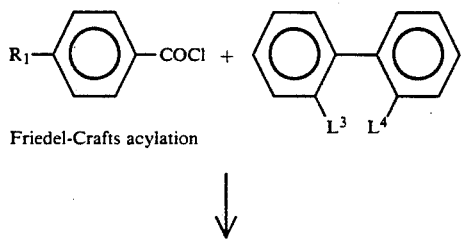

Friedel-Crafts acylation

Scheme 3:
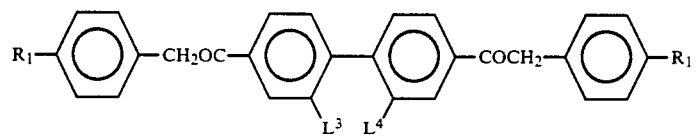
Huang-Minlon reduction
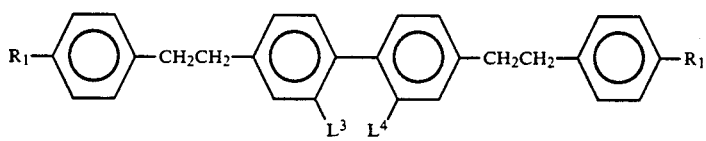
Scheme 4:
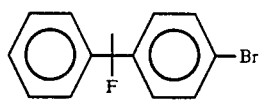
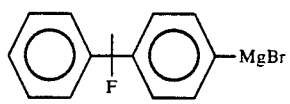
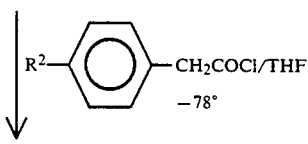
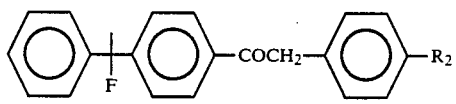
Huang-Minlon reduction
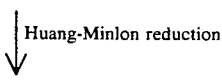
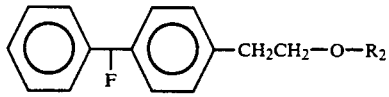
Friedel-Crafts acylation
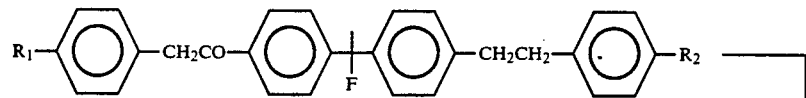
Huang-Minlon reduction
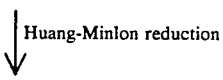
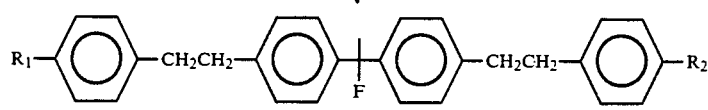
PCl₅

-continued
Scheme 4:
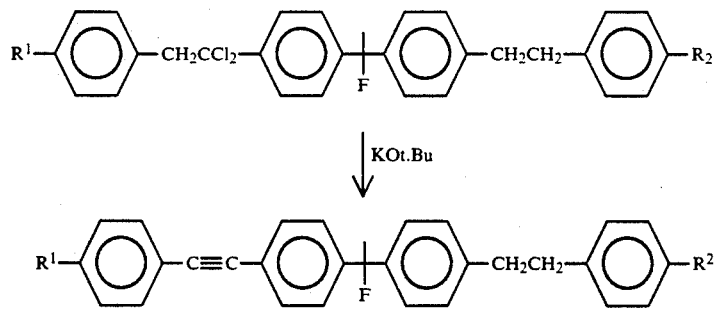
Scheme 5:
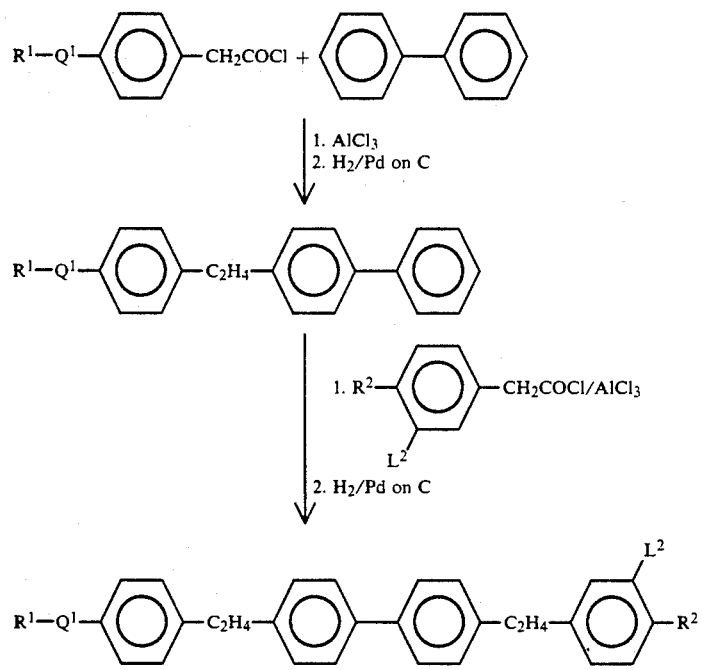
$R^2$ is preferably F, Cl, $CF_3$, $OCF_3$ or $OCHF_2$
$L^2$ = H or F.
Scheme 6:
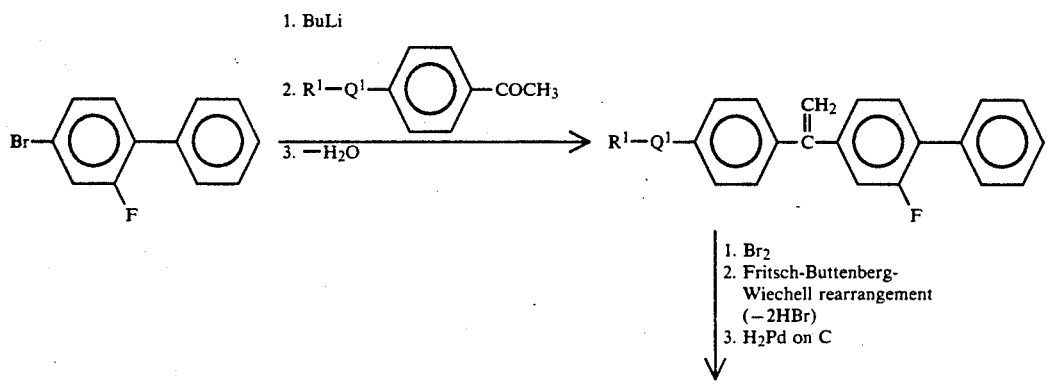
1. $Br_2$
2. Fritsch-Buttenberg-Wiechell rearrangement (−2HBr)
3. $H_2$Pd on C -continued Scheme 6:

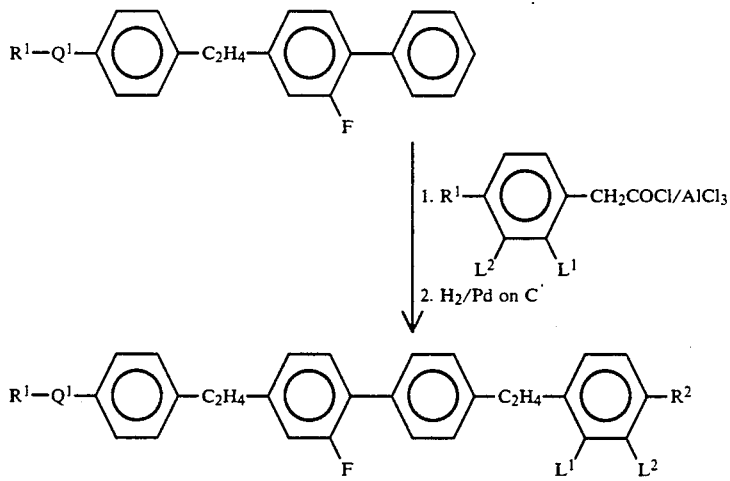

Scheme 7:

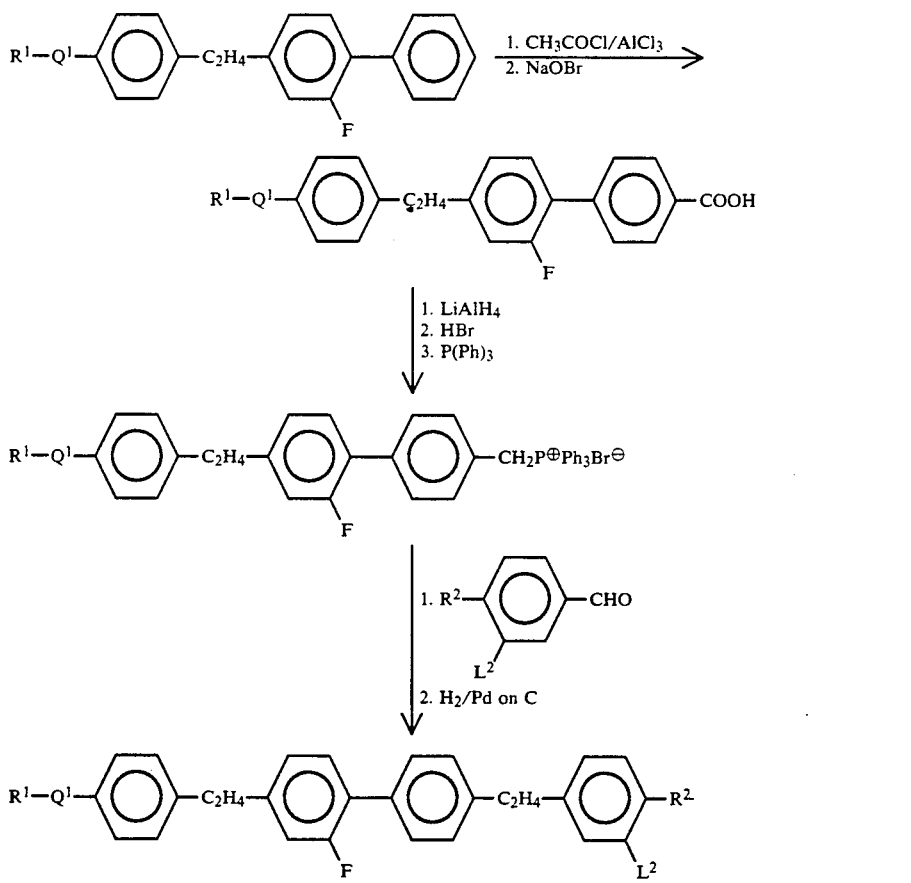

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention.

The other constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4,-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constitutents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed from —Phe—, —Cyc—, —Phe—Phe, —Phe—Cyc—, —Cyc—Cyc—, Pyr, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example pleochroic dyes can be added for the production of colored guest-host systems, or substances can be added to modify the dielectric anisotropy, the viscosity and/or the orientation of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, are hereby incorporated by reference.

m.p.=melting point, c.p.=clear point. "Customary work-up" means that water is added, the mixture is extracted with methylene chloride, the organic phase is separated off, dried and evaporated, and the product is purified by crystallization and/or chromatography.

In addition, the following abbreviations are used: C: crystalline solid state, S: smectic phase (the index denotes the phase type), N: nematic state, Ch: cholesteric phase, I: isotropic phase. The number between two symbols indicates the conversion temperature in degrees Celsius.

EXAMPLES

EXAMPLE 1

A solution of 0.2 g of CuCl and 0.5 g of hydroxylammonium hydrochloride in 16 ml of 50% aqueous ethylamine is added to a solution of 0.1 m of 4-fluorophenylacetylene in 100 ml of methanol. 0.1 m of p-n-pentylphenylbromoethyne dissolved in methanol is added dropwise under a nitrogen atmosphere and with stirring, the mixture is stirred for one hour, diluted with water and extracted with ether, and the extracts are washed until neutral. Customary work-up gives 1-p-n-pentylphenyl-4-p-fluorophenylbutadiyne.

EXAMPLE 2

Preparation of 4-n-pentyl-4'-(2-p-fluorophenylethyl)tolan

A) 0.1 m of 1-phenyl-2-(4-fluorophenyl)ethane is dissolved in 200 ml of $CH_2Cl_2$, and n-pentylbenzoyl chloride is added dropwise at 0°–5° C. (after addition of 0.1 m of $AlCl_3$). The mixture is stirred for a further 4 hours at room temperature, hydrolysed using $H_2O$ and worked up by extraction. The crude product is purified by crystallization.

B) 0.1 m of MeLi (in ether) is added dropwise at 0° C. to a solution in 200 ml of ether of 0.5 m of the ketone obtained. The mixture is stirred for a further 2 hours at room temperature, worked up by extraction and evaporated. The crude product is dissolved in toluene and boiled for 4 hours on a water separator with 1 g of p-toluenesulfonic acid. The mixture is worked up by extraction, and the crude product is purified by crystallization.

C) 0.05 m of the 1,1-diarylethene obtained is dissolved in ether, and $Br_2$ (0.05 m) is added dropwise at $-10°$ C. The mixture is evaporated, 100 ml of tert.-butanol and KOtBu (0.15 m) are added to the reaction product, and the mixture is boiled for 3 hours. The mixture is worked up by extraction, and the target product is purified by crystallization.

EXAMPLE 3

The compound 1,4-bis(p-n-propylphenylethyl)-2-fluorobiphenyl is obtained in accordance with scheme 4.

EXAMPLE 4

The compound 4-(p-n-propylphenylethyl)-4'-(3,4-difluorophenylethyl)biphenyl is obtained in accordance with scheme 5.

EXAMPLE 5

The compound 4-(p-n-propylphenylethyl)-4'-(2,3-difluoro-4-ethoxyphenylethyl)-2-fluorobiphenyl is obtained in accordance with scheme 6.

EXAMPLE 6

The compound 4-(p-n-propylphenylethyl)-4'-(p-trifluoromethoxyphenylethyl)-2-fluorobiphenyl is obtained in accordance with scheme 7.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A fluorine-containing aromatic compound of formula I

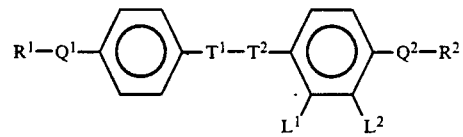

wherein $R^1$ is $C_{1-12}$-alkyl or $C_{1-12}$-alkenyl, $Q^1$ and $Q^2$ are each independently —O— or a single bond, or one of $Q^1$ and $Q^2$ is trans-1,4-cyclohexylene, $T^1$ is

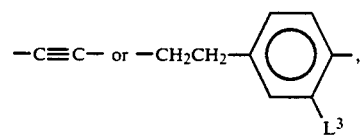

$T^2$ is

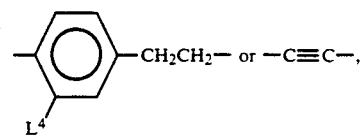

$R^2$ is F, Cl, —$CF_3$, —$OCF_3$, —$OCHF_2$ or one of the meanings of $R^1$, and $L^1$, $L^2$, $L^3$ and $L^4$ are each independently H or F, with the proviso that one and only one of $T^1$ and $T^2$ is —C≡C—.

2. A compound of the formula

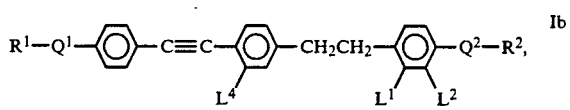

according to claim 1.

3. A compound of the formula

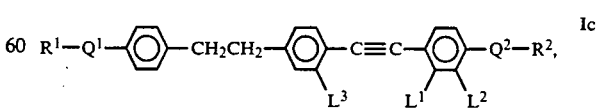

according to claim 1.

4. A liquid-crystalline phase containing at least two liquid-crystalline components, wherein at least one component is a compound of formula I

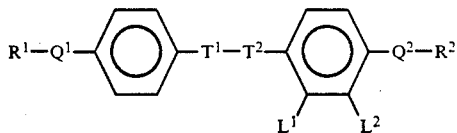

wherein $R^1$ is $C_{1-12}$-alkyl or $C_{1-12}$-alkenyl, $O^1$ and $O^2$ are each independently —O— or a single bond, or one of $O^1$ and $O^2$ is trans-1,4-cyclohexylene, $T^1$ is

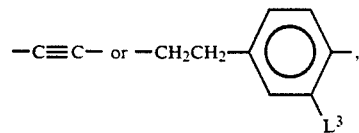

$T^2$ is

R² is F, Cl, —CF₃, —OCF₃, —OCHF₂ or one of the meanings of $R^1$, and $L^1$, $L^2$, $L^3$ and $L^4$ are each independently H or F, with the proviso that one and only one of $T^1$ and $T^2$ is —C≡C—.

5. A liquid-crystal display element containing a liquid-crystalline phase, wherein the phase is one of claim 4.

6. An electrooptical display element based on a liquid-crystalline dielectric, wherein the dielectric is a phase of claim 4.

* * * * *